Figure 1:
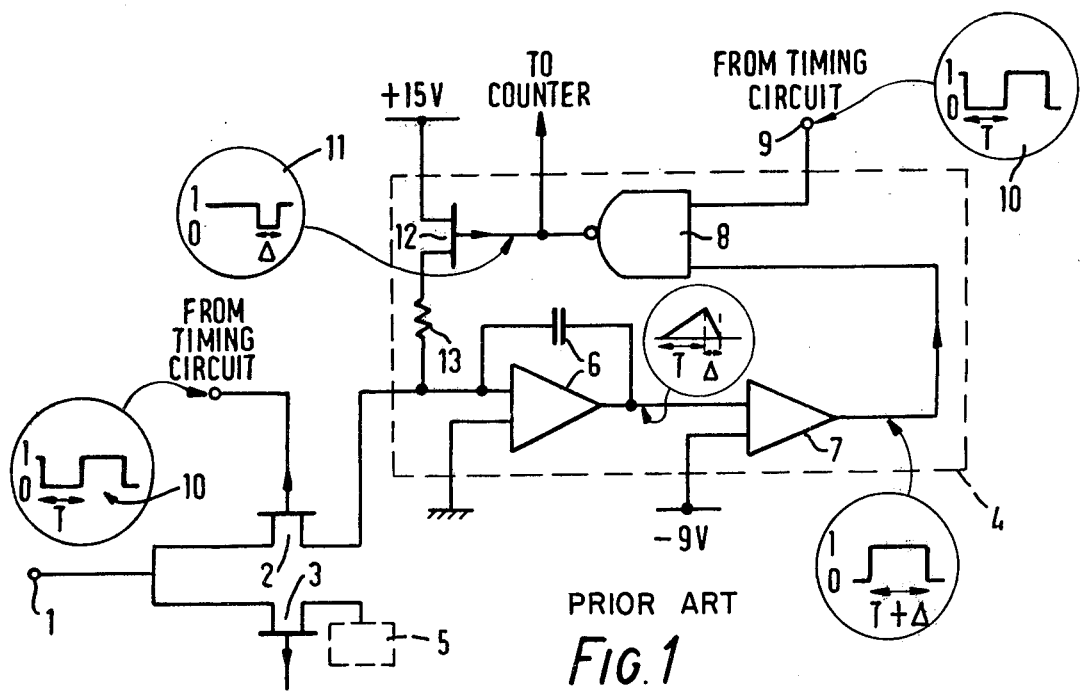

United States Patent [19]

Hounsfield et al.

[11] 4,160,954
[45] Jul. 10, 1979

[54] MULTIPLE RATE DISCHARGE CIRCUIT FOR INTEGRATOR, ESPECIALLY FOR USE IN COMPUTERIZED AXIAL TOMOGRAPHY

[75] Inventors: Godfrey N. Hounsfield, Newark; Richard G. Gillard, Uxbridge, both of England

[73] Assignee: E M I Limited, Hayes, England

[21] Appl. No.: 843,515

[22] Filed: Oct. 19, 1977

[30] Foreign Application Priority Data

Nov. 12, 1976 [GB] United Kingdom ............... 47143/76

[51] Int. Cl.$^2$ ........................... H03K 4/50; H03K 5/12
[52] U.S. Cl. ................................... 328/127; 328/142; 328/185; 307/294; 307/228
[58] Field of Search ............... 307/294, 228; 328/142, 328/127, 185

[56] References Cited

U.S. PATENT DOCUMENTS

| | | | |
|---|---|---|---|
| 2,849,609 | 8/1958 | Casey | 328/185 |
| 2,903,584 | 9/1959 | Jaffe et al. | 328/185 |
| 3,010,070 | 11/1961 | Siegel | 328/185 |

*Primary Examiner*—John S. Heyman

[57] ABSTRACT

A multiple rate discharge circuit is disclosed for application, for example, to an integrator connected to a radiation detector as used in computerized axial tomography. The integrator is charged for a given time and then allowed to discharge at a first, relatively slow, rate for a predetermined time. If, at the expiry of the predetermined time, charge remains in the integrator, the discharge rate is considerably increased. The second-mentioned discharge rate is preferably about eleven times faster than the just-mentioned rate, and the two rates are achieved by the selective connection of resistive discharge paths to the integrator.

6 Claims, 2 Drawing Figures

MULTIPLE RATE DISCHARGE CIRCUIT FOR INTEGRATOR, ESPECIALLY FOR USE IN COMPUTERIZED AXIAL TOMOGRAPHY

The present invention relates to electrical signal measuring arrangements, and it relates especially, though not exclusively, to such arrangements for use in that branch of radiography which has become known as computerised axial tomography (CAT).

In performing CAT, radiation has as X-radiation is projected through a cross-sectional slice of a body under examination along many substantially linear beam paths, and the absorption suffered by the radiation on traversing each of the paths is determined. The absorption values so determined are then processed in order to produce a representatin of the absorption (or transmission) coefficients, with respect to the radiation used, at each of many elemental locations distributed over the slice. Apparatus for performing CAT, and methods of operating the same, are described in U.S. Pat. No. 3,778,614.

The absorption along each of the afore-mentioned paths is determined by detecting the radiation transmitted through the body along the path and subtracting it from the amount of radiation projected into the body along that path. The detection of emergent radiation is conveniently achieved by means of one or more combinations of a scintillator crystal, which converts the X-radiation into light, and a photomultiplier tube which receives the light from the crystal and converts the light into an electrical signal.

The various beam paths are irradiated by scanning a source of the X-radiation relative to the body under examination, and each path is only irradiated briefly. Each crystal/photomultiplier combination is thus called upon to produce, in sequence, electrical signals representing the radiation transmitted through the body along a number of said paths, and problems arise in accurately measuring these signals, especially when the output signals have a large dynamic range, as is the case, for example, when the cross-sectional slice of the body which is under examination passes through the lungs, which of course contain considerable amounts of air.

It is an object of this invention to provide an electrical signal measuring arrangement which can accurately measure the amplitude of electrical signals having a large dynamic range.

According to the invention there is provided an electrical signal measuring arrangement comprising an integrator circuit connected to receive the signal to be measured, means for applying said signal to said integrator circuit for a predetermined time, means effective at the expiry of said time to cause said integrator circuit to discharge at a first rate, and means effective a predetermined period after said expiry to cause said integrator circuit to discharge at a second rate, faster than the first.

Figure 2:
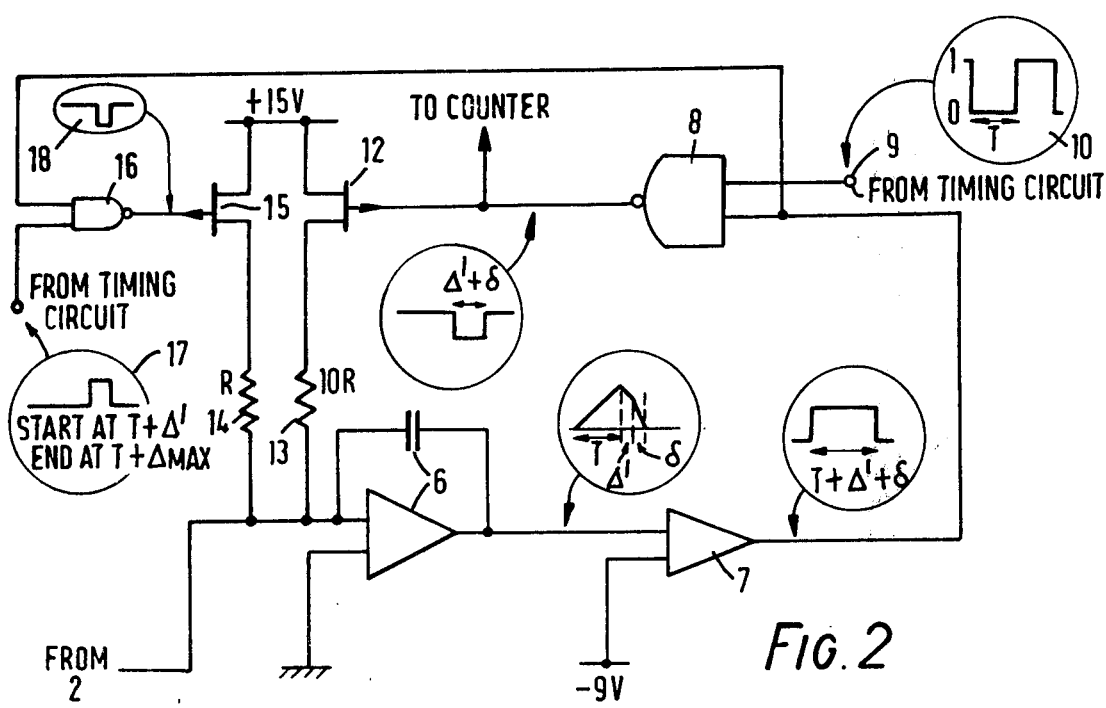

In order that the invention may be clearly understood and readily carried into effect, reference will now be made to the accompanying drawings, in which:

FIG. 1 shows the circuit diagram of a known measuring arrangement for electrical signals having a limited dynamic range of amplitudes, and FIG. 2 shows the circuit diagram of a measuring arrangement, in accordance with one example of the invention, for electrical signals having a wide dynamic range of amplitudes.

Referring now to FIG. 1, signals to be measured are applied via an input terminal 1 to a pair of field effect transistor switches 2 and 3. The switches feed respective measuring circuits 4 and 5, only the circuit 4 being shown in detail because circuit 5 is substantially identical thereto. Two circuits are used in this example because it is intended for use in a CAT apparatus and the signals relating to successively irradiated beam paths follow each other so rapidly that it is necessary for one circuit to measure the signal for one beam path whilst the other circuit produces an output indicative of the measured value of the signal relating to the previously irradiated beam path, and vice-versa.

The circuit 4 includes an integrator circuit 6, a level detector 7 connected to receive output signals from the circuit 6 and to produce a binary '1' signal so long as said output signals exceed zero potential, or some other threshold level. The detector 7 produces a binary '0' signal so long as the integrator output signals do not exceed zero or the threshold level as the case may be. The binary signals from detector 7 are applied to an AND gate 8, which also receives, via a terminal 9, integration pulses (such as those shown at 10) from a master timing circuit (not shown); the integration pulse also being binary and having the value '0' during the integration time of integrator 6 and the value '1' during the output signal production time for circuit 4, this time being the same as the integration time for the integrator, corresponding to circuit 6, included in circuit 5.

The integration pulses 10 are also applied to the switch 2, causing it to route the signals from terminal 1 to integrator 6 while the pulses 10 have the value '0'. The 'AND' gate 8 produces an output pulse 11 only when both of the signals applied to its input terminals have the binary '1' value, namely during the time between the end of the integration period for integrator 6 and the decay of the charge stored in the integrator to zero (or the threshold).

The decay is controlled by a field effect transistor switch 12 which is enabled by the pulse 11 and opens a discharge path for the integrator 6 through a resistor 13. Clearly, once the charge stored in the integrator has decayed to zero, or the threshold level as the case may be, the level detector output reverts to binary '0' thus turning off the AND gate 8 and disabling the discharge path through resistor 13. The circuit 4 is then in readiness for another integration period.

The pulse 11, as well as controlling the discharge of circuit 6, is applied to a counter (not shown) which counts clock pulses of a predetermined frequency, applied thereto from the aforementioned master timing circuit, for the duration of the pulse 11. The count held in the counter at the termination of a pulse 11 is thus a measure of the amount of charge stored in the integrator 6 during the immediately preceding integration period, and is thus a measure of the amplitude of the input signal applied to the circuit 4 during that period.

As mentioned previously, however, although this circuit has been shown to work well in practice, it works best with signals of limited dynamic range. This is because a predetermined maximum count (typically 8192) has to be set in order that the circuit 4 and the associated counting circuit can be re-set in time to receive the next input signal, and this limits the maximum amplitude of signals which can be measured.

In accordance with one example of the invention, a circuit of the kind shown at 4 in FIG. 1 is modified to enable it to handle signals of larger dynamic range.

Referring now to FIG. 2, which shows one embodiment of the invention, components similar to those already described in relation to FIG. 1 bear the same reference numbers and will not be further described.

The value of the resistor 13 in the FIG. 2 arrangement is 10R, and this is shunted by the series connection of a resistor 14 of resistance R and a field effect transistor switch 15. The switch 15 is controlled by the binary output from an AND gate 16 which receives the binary output signal provided by level detector 7 and a binary clock pulse 17, derived from the aforementioned master timing circuit (not shown) and arranged to start a fixed time $\Delta'$ after the integration pulse 10 has assumed the binary value '1', said fixed time $\Delta'$ being equivalent to a count of (say) 4096 in the aforementioned counter (not shown). If the output of detector 7 is still in the '1' condition when the pulse 17 commences, and remains so for a period $\delta$, the AND gate 16 produces an output pulse 18, of duration $\delta$, which enables the field effect transistor switch 15, thus causing the integrator 6 to discharge through the resistor 14 as well as the resistor 13. This causes the discharge rate to increase eleven fold so that charge can be dissipated from the integrator much more rapidly than in the arrangement shown in FIG. 1. Thus, although the maximum discharge time ($\Delta$max) remains fixed and is, of course, less than or equal to T, the circuit of FIG. 2 can deal with substantially higher values of charge (and thus of input signal amplitude) than can the circuit of FIG. 1.

For example, in the circuit of FIG. 1, if the counter reading is 6000, then that represents the value of the input signal during the relevant integration period. However, in the arrangement of FIG. 2, because the discharge rate is increased eleven-fold after a count of 4096 has been reached, a count of 6000 actually represents an input signal count of 4096+11(6000−4096), that is 25,040. The maximum input signal count that can be represented in this example is 4096+11(8192−4096), or 49,152.

Clearly, the accuracy in the range 4097 to 8192 is reduced compared with the FIG. 1 arrangement.

Clearly also, other arrangements could be proposed which do not accord with the description given above but nevertheless are within the scope of the invention. Moreover the numerical values mentioned above are referred to by way of example only.

A particularly advantageous application of the invention, although not of course the only one, resides in its use in association with a CAT apparatus which is employed for scanning the heart of a human patient. It has been disclosed, for example in U.S. Pat. Nos. 3,952,201 and 4,126,785 that when scanning a slice of a body including the heart, it is advantageous to synchronise the scanning with the movements of the heart so that radiation is passed through the heart only when it assumes a predetermined position or a predetermined range of positions. The disclosures of the two patent applications referred to above are incorporated herein by reference, and thus the actual scanning apparatus will not be more fully described herein.

What we claim is:

1. An electrical signal measuring arrangement comprising:
   (a) an integrator circuit connected to receive the signals to be measured,
   (b) means for applying said signals to said integrator circuit for a predetermined charge period (T)
   (c) means, effective from the expiry of said period (T), to cause said integrator to discharge at a first rate, and including an electrically resistive discharge path connected to said integrator circuit by way of a switchable means for enabling or disabling said path, and control means for generating a control signal for controlling said switchable means, the control means including
      (i) a comparing means for comparing the instantaneous output of said integrator circuit with a reference value and providing an output signal when said instantaneous output exceeds said reference value,
      (ii) an AND gate connected to receive the output signal from said comparing means and an electrical waveform defining charge and discharge periods for said integrator circuit and generating said control signal, and
      (iii) means for applying said control signal to said switchable means to enable said path only when the output of said integrator circuit exceeds said reference value during said discharge periods, and
   (d) means effective from the expiry of a predetermined time $\Delta'$ following the expiry of the charge period (T) to cause said integrator circuit to discharge at a second rate, faster than the first-mentioned rate;
   wherein said means effective to cause said integrator circuit to discharge at said second rate includes said resistive discharge path, said switchable means and said control means and, in addition, a further electrically resistive discharge path, of lower resistance than said first-mentioned path and connected in parallel therewith, a further switchable means, for enabling or disabling said further path, and a further control means for generating a further control signal for controlling said further switchable means.

2. An arrangement according to claim 1 wherein said further control means includes said comparing means and an AND gate connected to said comparing means and to a source of an electrical waveform which assumes a predetermined value once said predetermined period has elapsed after said expiry, and means for applying said further control signal to said further switchable means to enable said further path only when said last recited electrical waveform assumes said predetermined value and said integrator circuit output exceeds said reference value.

3. An arrangement according to claim 1 wherein said switchable means comprises a transistor switch connected in series in said path.

4. An arrangement according to claim 1 wherein said further switchable means comprises a transistor switch connected in series in said further path.

5. A circuit arrangement for evaluating the magnitude of analogue input signals, the arrangement comprising an input terminal for said input signals, an integrating device, switchable means for selectively connecting said terminal to said integrating device, a threshold device connected to receive output signals from said integrating device and arranged to produce an enabling signal as long as the magnitude of said output signals exceeds a reference magnitude, first and second leakage paths for said integrating device, each leakage path having associated therewith a respective switchable means for selectively connecting the paths to the integrating device in response, inter alia, to said enabling signal, and means responsive to timing signals to control the operation of the various switchable means, and causing, in operation of the circuit arrangement:

(a) the connection of said input terminal to said integrating device for a predetermined time period (T), followed by (b) the disconnection of said terminal from said integrating device, and the connection of the first leakage path to said integrating device, said connection persisting until said enabling signal is discontinued, and (c) the connection of said second leakage path to said integrating device a predetermined time ($\Delta'$) after the connection of said first leakage path thereto, unless said enabling signal has previously been discontinued; the leakage from the said integrating device occuring more rapidly after connection of said second leakage path to said integrating device than before such connection.

6. A circuit arrangement according to claim 5 wherein the ratio of the rates of leakage from said integrating device after and before the connection of said second leakage path to said integrating device is about 11:1.

* * * * *